United States Patent [19]

Kelsey et al.

[11] 4,305,829
[45] Dec. 15, 1981

[54] PROCESS FOR FLOCCULATING AN AQUEOUS SUSPENSION OF PARTICLES WITH QUATERNARY AMMONIUM GRAFT COPOLYMERS

[75] Inventors: Donald R. Kelsey; Russell L. Kreeger, both of Hillsborough, N.J.

[73] Assignee: Union Carbide Corporation, New York, N.Y.

[21] Appl. No.: 156,732

[22] Filed: Jun. 5, 1980

Related U.S. Application Data

[62] Division of Ser. No. 53,193, Jun. 29, 1979.

[51] Int. Cl.³ .................... C02F 1/56; B01D 21/01
[52] U.S. Cl. .................................... 210/736; 210/735
[58] Field of Search .................. 210/732, 735, 736; 260/29.2 EP, 567.6 P; 525/523; 528/407; 544/358

[56] References Cited

U.S. PATENT DOCUMENTS

| | | | |
|---|---|---|---|
| 3,567,659 | 3/1971 | Nagy | 260/2 |
| 3,632,507 | 1/1972 | Witt | 210/735 |
| 3,663,461 | 5/1972 | Witt | 260/29.2 EP |
| 3,725,312 | 4/1973 | Panzer et al. | 260/2 BP |
| 3,778,476 | 12/1973 | Rembaum et al. | 260/567.6 P |
| 3,898,188 | 8/1975 | Rembaum et al. | 260/2 R |
| 3,917,817 | 11/1975 | Vanlerberghe et al. | 260/2 EP |
| 3,927,242 | 12/1975 | Rembaum et al. | 260/2 R |
| 3,928,448 | 12/1975 | Ballweber et al. | 260/29.6 R |
| 4,054,542 | 10/1977 | Buckman et al. | 260/2 BP |

FOREIGN PATENT DOCUMENTS

2323886 11/1973 Fed. Rep. of Germany .

OTHER PUBLICATIONS

*Chemical Abstracts*, vol. 80, No. 22, 6/1974, p. 100, (135058x).

*Primary Examiner*—Peter A. Hruskoci
*Attorney, Agent, or Firm*—Donald M. Papuga

[57] ABSTRACT

Described herein is a process for flocculating an aqueous suspension of finely divided particles which comprises treating the suspension with an effective amount of a water-soluble graft copolymer to achieve the desired degree of flocculation of said particles, said water soluble graft copolymer being comprised of polymeric units characterized by the general formula:

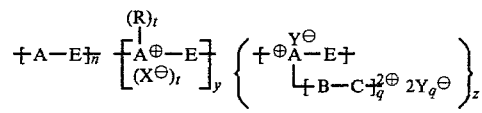

wherein n, y and z represent the relative molar equivalent fractions of each of the respective polymeric units in the graft copolymer, the sum of n, y and z being 1.0, the value of n varying from 0.00 to 0.99, the value of y varying from 0.00 to 0.99 and the value of z varying from 0.01 to 0.99; q is an integer greater than 1; A is the unit derived from at least one difunctional amine selected from the group consisting of primary amines and di(secondary)amines; t is an integer varying from 1 to 2; E is the unit obtained from a compound selected from the group consisting of epihalohydrins and diepoxides after its reaction with said difunctional amine; R is an organic radical derived from a quaternizing agent having the general formula RX, where X is the residual counter ion formed after quaternization; B is the unit derived from an organic dihalide having the general formula $BY_2$, where Y is $Cl^-$, $Br^-$ or $I^-$ with the proviso that such halogens are not attached to the same carbon atom; and C is the unit derived from an organic di(tertiary)amine after its reaction with said organic dihalide.

6 Claims, No Drawings

PROCESS FOR FLOCCULATING AN AQUEOUS SUSPENSION OF PARTICLES WITH QUATERNARY AMMONIUM GRAFT COPOLYMERS

This application is a division of our prior U.S. application Ser. No. 53,193, filed June 29, 1979.

The present invention relates to novel cationic graft copolymers, their method of preparation and their use as flocculants. More particularly, the present invention relates to quaternary ammonium graft copolymers prepared by grafting quaternary ammonium ionene-type polymeric side chains onto a polymer backbone formed by the reaction of a difunctional amine and an epihalohydrin or diepoxide.

Flocculation, or the clarification of aqueous suspensions, is an increasingly important commercial and governmental operation. Its primary object is to permit water purification, conservation or reuse and to insure that contaminated aqueous streams be made acceptable for discharge. It encompasses the clarification of industrial process streams, such as those generated in mining operations, as well as the clarification of bodies of water, such as river water, which contain industrial and municipal waste materials. In iron ore mining, for example, the relatively low grades of ore which are generally available necessitate the use of beneficiation processes in order to produce a usable grade of ore. Such processes result in the production of large volumes of water containing suspended minerals. The necessity of clarifying such aqueous suspensions for reuse or discharge, combined with the increasing public concern with environmental pollution and contamination have underscored the need for efficient and economic flocculant materials for the removal of suspended matter from aqueous streams.

Traditional flocculants such as alum, starch and iron salts have been replaced in many areas of waste water treatment by more efficient organic polymer flocculants. U.S. Pat. No. 3,725,312 discloses the use of polyquaternary compounds produced by the reaction of methylamine and epichlorohydrin for use as flocculants. u.S. Pat. Nos. 3,928,448 and 3,632,507 disclose ionene-type polymers for water clarification applications. U.S. Pat. No. 3,567,659 relates to graft polymers wherein a vinyl polymeric side chain is grafted onto a methylamine-epichlorohydrin backbone polymer. The cationic polymer thus formed is said to be a useful flocculant. U.S. Pat. No. 4,054,542 relates to cationic water-soluble branched ionene-type polymers for use as flocculants. Although such organic flocculants are often effective in various applications, there exists a need for more efficient flocculants so as to lower the cost of water clarification and/or reduce the amount of flocculant which is introduced into the environment as a result of such water treatment.

The present invention is directed to a process for flocculating an aqueous suspension of finely divided particles which comprises treating the suspension with an effective amount of a water-soluble graft copolymer to achieve the desired degree of flocculation of said particles, said water soluble graft copolymer being comprised of polymeric units characterized by the general formula:

SUMMARY OF THE INVENTION

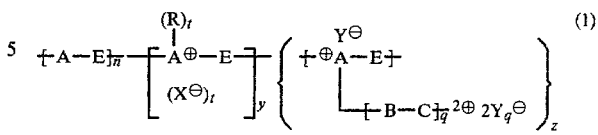

wherein n, y and z represent the relative molar equivalent fractions of each of the respective polymeric units in the graft copolymer, the sum of n, y and z being 1.0, the value of n varying from 0.00 to 0.99, the value of y varying from 0.00 to 0.99 and the value of z varying from 0.01 to 0.99; q is an integer greater than 1; A is the unit derived from at least one difunctional amine selected from the group consisting of primary amines and di(secondary)amines; t is an integer varying from 1 to 2; E is the unit obtained from a compound selected from the group consisting of epihalohydrins and diepoxides after its reaction with said difunctional amine; R is an organic radical derived from a quaternizing agent having the general formula RX, where X is the residual counter ion formed after quaternization; B is the unit derived from an organic dihalide having the general formula $BY_2$, where Y is $Cl^-$, $Br^-$ or $I^-$ with the proviso that such halogens are not attached to the same carbon atom; and C is the unit derived from an organic di(tertiary)amine after its reaction with said organic dihalide.

For the preferred graft copolymers of the invention, the value of n varies from about 0.1 to 0.80, the value of y varies from about 0.2 to 0.7 and the value of z varies from about 0.01 to 0.6.

The graft copolymers are prepared by reacting at least one difunctional amine selected from the group consisting of primary amines and di(secondary)amines and a compound selected from the group consisting of epihalohydrins and diepoxides in the presence of a base to form a water-soluble backbone polymer, such polymer then being reacted with a di(tertiary)amine and an organic dihalide to form the quaternary ammonium graft copolymer.

The above-described graft copolymers are used to flocculate aqueous suspensions of finely divided particles by a method which comprises treating the aqueous suspension with an effective amount of the water-soluble graft copolymer to achieve the desired degree of flocculation. Other applications of such quaternary ammonium graft copolymers include their use as antimicrobial agents, paper sizing agents, oil recovery aids, boiler additives and as additives in skin care products.

The term "RV" as used throughout the specification refers to the reduced viscosity measured at 0.2 grams polymer in 100 milliliters of 1.0 molar NaCl solution at 25° C.

DETAILED DESCRIPTION OF THE INVENTION

The graft copolymers of the invention comprise ionene-type side chains, namely, polymers containing quaternary ammonium groups, grafted onto a difunctional amine-epihalohydrin or diepoxide polymeric backbone.

The reaction scheme illustrating the three steps which are generally involved in the synthesis of of such graft copolymers are shown in equations (2) to (4) as follows:

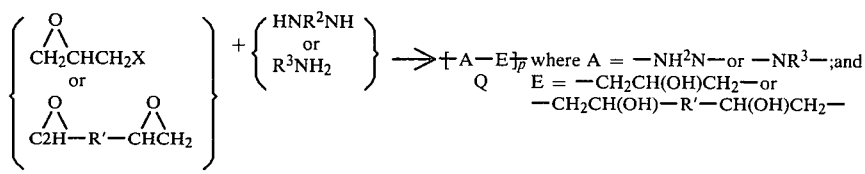  (2)

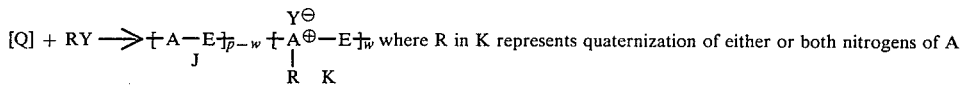  (3)

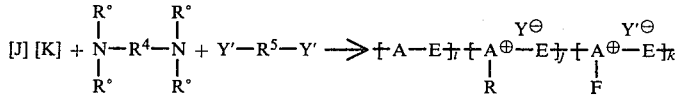  (4)

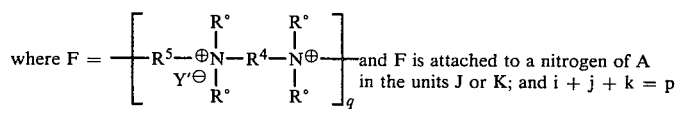

Equation (2) shows the reaction between an epihalohydrin and/or diepoxide with difunctional amine. Generally, approximately a molar equivalent of base relative to the epihalohydrin is used for the reaction.

Equation (3) depicts the quaternization step of some of the tertiary amino groups of the backbone polymer of equation (2). The extent of quaternization will generally be dependent upon the number of tertiary amino groups in the polymer and the molar amount of quaternizing agent (RY) used relative thereto. Statistically, one can expect that each type of amino group in the polymer can be quaternized to some degree; indeed all of them in a given polymer repeating unit may be quaternized, even though the molar amount of the quaternizing agent used is theoretically insufficient to quaternize all of the tertiary amino groups in the polymer. Thus, the formula for the polymers of this invention are intended to reflect a random, symmetrical or unsymmetrical quaternization, and for that reason R is not shown bonded to any particular tertiary nitrogen in the polymer. Although the quaternization step of equation (3) is preferred, it may be omitted and the graft copolymer formed directly from the unquaternized polymer of equation (2) as hereinafter discussed.

Equation (4) shows grafting of the quaternized polymer of equation (3). In this reaction, the quaternized polymer of equation (3) is reacted concurrently with a di(tertiary)amine and a dihalohydrocarbon. In this reaction, generally an amount of di(tertiary)amine is used which is insufficient to react with all of the reactive halogen groups in the dihalohydrocarbon. In general, the degree of grafting will depend upon the relative amounts of the three reactants, the degree of quaternization of the polymer backbone of equation (3), and the specific reaction conditions of choice including the normal rules of stoichiometry and reaction kinetics.

In a preferred embodiment of the invention, the polymer backbone is poly(N-glycidylpiperazine) formed by the reaction of piperazine and epichlorohydrin in the presence of a base such as NaOH. The polymer backbone is then partially quaternized and then grafted with a polymeric side chain resulting from the reaction of 1,3-bis(dimethylamino)-2-propanol and 1,4-dichloro-2-butene.

The polymeric units of the resulting graft copolymer are characterized as follows:

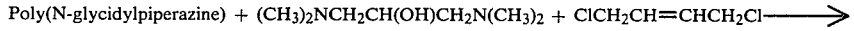  (5)

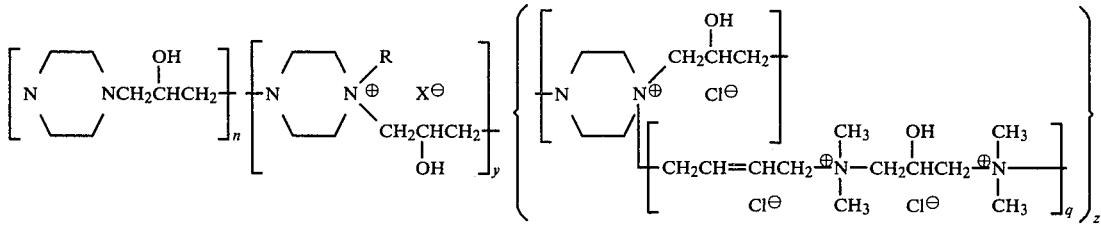

wherein n, y, q, z and R are as defined in equation (1).

The quaternization of the polymer backbone as illustrated in equation (3) is readily carried out by reacting the condensation product resulting from equation (2) with a suitable quaternization agent in a solvent such as aqueous methanol. The choice of quaternization agent is not critical and encompasses those compounds known in the art to be capable of quaternizing tertiary nitrogens. Organic compounds such as alkyl, alkenyl, arylalkyl, and cycloalkyl halides or sulfates may be used for this purpose. Among the halogen compounds, chlorides and bromides are preferred from the standpoint of availability and reactivity. Fluorides are generally not used. Suitable quaternizing agents include alkyl halides and sulfates having 1–18 carbon atoms, branched or linear, unsubstituted or having substituents such as F, $NO_2$ and phenyl; cycloalkyl halides and sulfates having 4 to 18 carbon atoms, unsubstituted or having substituents such as F, $NO_2$ and phenyl; substituted or unsubstituted alkenyl halides and sulfates having 3–18 carbon atoms. Particularly preferred quaternizing agents include allyl chloride, methyl chloride, methyl iodide, benzyl chloride and lower alkyl sulfates.

The percent of quaternization of the polymer backbone, i.e., the percent of A units containing one or more quaternary nitrogens as shown in equation (3) above, may vary from about 0 to 99 percent, more typically from 0 to 80 percent and preferably from 20 to 70 percent depending upon the ratio of polymer backbone to polymeric side chain constituents which are reacted in in equation (4) to form the final graft copolymer. If the percent of quaternization is too low, excessive cross-linking may occur when forming the graft copolymer, particularly when a large proportion of backbone polymer is used in equation (4); conversely, if the percent of quaternization is too high, the number of available tertiary nitrogens on the backbone is reduced and little or no grafting may result, particularly when a small proportion of backbone is used in equation (4). Thus, for example, when no quaternization (as per equation (3) above) is effected, the polymer backbone may consitute about 1–15 weight % of the final product. At about 40 percent of quaternization (as per equation (3) supra) or greater, the ratio of backbone to side chain should be at least 1:10 in order to effect an appreciable amount of grafting. Preferably, the percent of quaternization varies from 20 to 70 percent with a range of 40 to 70 percent being most preferred. The percent of quaternized nitrogens in [J] [K] of equation (3) can be readily determined by the increase in the product wweight relative to the starting material, or by standard halide analyses. Correspondingly, the preferred range of backbone in the graft copolymer is from about 5 to 50 weight percent of the final product.

The preparations of poly[N-glycidylpiperazine] (NGP) and its partially quaternized derivative are disclosed in the art, such as in Examples 1 and 3 of U.S. Pat. No. 3,917,817. In general, the NGP polymer contains epoxy or chloro end groups (see U.S. Pat. No. 2,963,483 for an illustration of such end groups in N-glycidylpiperazine monomer) which can undergo further reaction and possibly result in highly crosslinked material as disclosed in U.S. Pat. No. 4,018,721. For purposes of the present invention, a water-soluble, non cross-linked NGP polymer backbone having a reduced viscosity (RV) of from about 0.1 to about 0.8 is required. An RV of from about 0.2 to 0.5 is generally preferred. The RV is a function of the molar ratio of epichlorohydrin to piperazine and reaction time and temperature.

The backbone polymers of the invention, particularly in unquaternized form, generally tend to react and form a gel with the passage of time due to the presence of the aforementioned epoxy or halide end groups. It is therefore preferable to stabilize the backbone subsequent to its formation, particularly if it is to be stored for an appreciable length of time prior to the graft reaction, by reacting the residual epoxy or halide end groups in the backbone polymer with a sufficient amount of a primary or secondary amine so as to prevent cross-linking from occurring. Capping of the end groups in this manner may be conveniently carried out by reacting an amine such as dimethylamine with the polymer backbone at a temperature of about 50° C. for about 1 hour. If a greater than stoichiometric amount of amine is used for the reaction, it is desirable that it be removed from solution, such as by distillation, prior to the grafting step. A slightly greater than stoichiometric amount of amine is generally preferred for this reaction with subsequent removal of the excess.

The dihalide and di(tertiary)amine components of the polymeric sidechain (from which the units B and C are derived, respectively, in the general formula (1) above) may be selected from a wide variety of compounds in accordance with the invention. In general, the tertiary amine groups of the diamines should be separated by at least two carbon atoms and the halogens in the dihalide should not reside on the same carbon atom. In some cases, however, even with two or more atoms separating the nitrogens of the amine groups and the halides, the product of their reaction may be a cyclic dimer, trimer or other undesirable low molecular weight product. Accordingly, the dihalide and diamine are selected such that they form a polymeric product under the reaction conditions chosen for the preparation of the graft polymer, but in the absence of the polymeric backbone substrate. That is, the diamine and dihalide must be polymerizable independently of the backbone polymer. For the present invention, the polymeric sidechain products thus produced should have a molecular weight sufficient to give an RV of at least 0.05.

The di(tertiary)amines useful for forming sidechain polymers in accordance with the present invention are characterized by the formula:

wherein $R_3$ is a two or more carbon-atom radical selected from among alkyl radicals of from 2 to about 20 carbon atoms which may be branched or unbranched, cyclic or acyclic, substituted or unsubstituted, or containing hetero atoms such as O, S or aryl groups; aryl radicals consisting of from 6 to about 20 carbon atoms substituted or unsubstituted; and arylalkyl or alkylaryl radicals containing 7 to 20 carbon atoms, substituted or unsubstituted; and $R_1$, $R_2$, $R_4$, and $R_5$ are selected from among alkyl radicals consisting of from 1 to about 20 carbon atoms, more usually from 1 to 10 carbon atoms, which may be branched or unbranched, cyclic or acyclic, substituted or unsubstituted, or containing hetero atoms such as O, S or aryl groups; and aryl radicals consisting of from 6 to about 20 carbon atoms, more usually from 6 to about 10 carbon atoms, substituted or unsubstituted; and arylalkyl or alkylaryl radicals containing 7 to 20 carbon atoms, substituted or unsubstituted; the individual R's connected to a common or different nitrogen may be interconnected to form one or more cycloaliphatic or aromatic rings which may or may not contain hetero-atoms such as O, S and the like.

$R_1$ through $R_5$ may be connected to each other in pairs or in multiple arrangements. Thus, for example, where $R_3$ is ethylene ($-CH_2CH_2-$), $R_2$ and $R_5$ are each methyl and $R_1$ and $R_4$ are connected to each other and are each methylene, the di(tertiary)amine is N,N'-dimethylpiperazine. Similarly, where $R_3$ is ethylene, and $R_1$ and $R_4$, and $R_2$ and $R_5$ are connected to each other in pairs and are each methylene, the diamine is 1,4-diazabicyclo[2.2.2.]octane; and where $R_3$ is ethylene and $R_1$ and $R_2$, and $R_4$ and $R_5$ are connected to each other in pairs and are each ethylene, the diamine is 1,2-ethylenedipyrrolidine.

Other useful diamines include the following: $(CH_3)_2NCH_2CH_2CH_2CH(OH)CH_2N(CH_3)_2$; $(CH_3)_2NCH_2CH_2OCH_2CH_2N(CH_3)_2$; $(CH_3)_2NCH_2CH_2CH_2CH(CH_3)N(CH_3)_2$; $(CH_3)_2NCH_2C_6H_4CH_2N(CH_3)_2$; 4,4'-bipyridine; and 1,3-propylene-N,N-dimorpholine.

Among the dihalides useful for the present invention are the following: $ClCH_2CH=CHCH_2Cl$; $(ClCH_2CH_2)_2O$; $BrCH_2CH_2CH_2Br$; $CH_2=CHCH(Cl)CH_2Cl$; $ClCH_2CH_2Cl$; $BrCH_2CH(OH)CH_2Br$; $ClCH_2C_6H_4CH_2Cl$; $(ClCH_2CH_2OCH_2)_2$; and 3,5-dihalocyclopentene. A particularly preferred dihalide is 1,4-dichloro-2-butene having a high trans isomer content. The dihalide may contain mixtures of halogens and may also contain unreactive halogens such as fluoride or vinyl halide.

Preferred combinations of diamines and dihalides to form polymeric sidechains include 1,3-bis(dimethylamino)-2-propanol and 1,4-dihalo-2-butene and 1,3-bis(dimethylamino)butane and α,α'-dihalo-p-xylene.

In general, the molar ratio of diamine to dihalide should be about 0.90 to 1.10. A very slight excess of dihalide is usually preferred.

The difunctional amine component of the backbone polymers of the invention (from which A is derived in the general formula (1) above) may be characterized by the formulae:

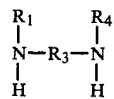 (7)

and $R_6NH_2$ (8)

wherein $R_1$, $R_3$ and $R_4$ are as defined above in formula (6) with regard to the di(tertiary)amine, except that $R_3$ may also be a one-carbon atom radical and $R_6$ is similarly defined as $R_1$.

Thus, for example in formula (7) where $R_1$ and $R_4$ are methyl and $R_3$ is ethylene, the diamine is N,N'-dimethylethylenediamine; and where $R_3$ is ethylene and $R_1$ and $R_4$ are connected to each other and are methylene, the diamine is piperazine.

Other suitable difunctional amines include the following: $CH_3NH(CH_2)_4NHCH_3$, $CH_3NHC_6H_4NHCH_3$, 1,3-diazacyclopentane, methylamine, ethylamine, aniline, cyclohexylamine, isopropylamine and benzylamine.

The unit E of formula (1) above is derived from a epihalohydrin or diepoxide after it has reacted with the aforementioned difunctional amine to form a backbone polymer in accordance with the invention. Epihalohydrin monomers have the formula:

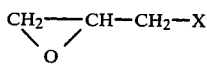 (9)

where X is Cl, Br, I or F. For purposes of the invention X is preferably Cl or Br, with epichlorohydrin being the particularly preferred epihalohydrin.

Suitable diepoxides are those organic compounds containing two (2) epoxy groups such as those derived from the epoxidation of polyethylenically unsaturated compounds, the reaction of epihalohydrin and diols or primary and/or secondary diamines and the like. The epihalohydrin reaction is commonly carried out in the presence of a strong base to convert the dihalohydrins to the desired diepoxide. Examples of suitable diepoxides are the diglycidyl ether of bisphenol-A, N,N'-diglycidylpiperazine, N,N'-diglycidylaniline, butadiene-1,4-diepoxide, epoxidized soybean oil, and polymers of the foregoing which are terminated by terminal (or vicinal) epoxy groups.

PROCESS DISCUSSION

The formation of the polymer backbone as described above by the reaction of an epihalohydrin or diepoxide with a difunctional amine is carried out under conditions known in the art for forming water-soluble N-glycidyl polymers. In general, the reaction is carried out in substantially alcoholic solvents at a temperature of from about 0° to 150° C., preferably from about 25° C. to 80° C., in the presence of caustic alcohol. The molar equivalent ratio of the epihalohydrin or diepoxide to the difunctional amine is typically from about 0.9 to about 1.2. The caustic alcohol is generally added to the solvent in an amount from about 0.9 to 1.1 equivalents based on the amount of epihalohydrin. After reacting for about ½ to 24 hours, the solution is preferably filtered to remove any inorganic salts formed. Thereafter, the molecular weight of the polymer can be increased by heating the solution to a temperature of from about 30° to 100° C. If the polymer backbone is to be quaternized prior to the grafting reaction, the quaternizing agent is then added to the polymer solution and allowed to react at at temperature of from about 25° to 125° C. for a period of about ½ to 24 hours. The polymer is then preferably stabilized at this point by heating with an amine such as dimethylamine.

Grafting of the polymer backbone is carried out by reacting the organic dihalide with a mixture of di(tertiary)amine and polymer backbone at a temperature of from about 25° C. to 125° C., preferably 50° C. to 70° C. The polymer backbone may comprise about 1-95 percent of the total reactants which form the graft copolymer, but is preferably about 1-50 percent. The ratio of di(tertiary)amine to dihalide is typically about stoichiometric but may range from about 1.0:0.9 to 0.9:1.0. A preferred method of reaction is to effect rapid addition of about 80 to 90 weight percent of the dihalide to the reaction mixture followed by dilution of the reaction with water or other solvent to about 20 weight percent solids, and the remaining 10 to 20 percent of the dihalide then added incrementally. The reactions may be effected under atmospheric or superatmospheric pressures, or under an inert atmosphere such as nitrogen.

The above reactions describing the preparation of the polymer backbone are preferably carried out in a substantially alcoholic solvent such as aqueous methanol or ethanol, while water or a substantially aqueous solvent is preferably used for the graft copolymer reaction. The intermediate polymeric products, i.e., quaternized or unquaternized polymer backbone, may be isolated if desired prior to the grafting reaction, but it is generally more convenient to form the graft copolymer in situ directly from the unisolated polymer backbone. In situ formation refers to the substitution of water or an aqueous solvent for the alcoholic solvent used in the preparation of the backbone prior to the grafting reaction while maintaining the intermediate polymeric products in solution. This is conveniently accomplished by adding the aqueous solvent to the reaction mixture containing alcohol, preferably in increments, followed by removal of alcohol by distillation, such addition and distillation steps being repeated as needed until the desired amounts of alcohol and aqueous solvent are removed and added, respectively.

Following preparation of the graft copolymer it is preferably stored in an aqueous solution having a pH of from about 4 to 6 until it is used.

Table I below presents flocculation data for the various polymers prepared in the Examples which follow. The control examples designated by a letter refer to the preparation of described polymeric backbones or sidechains; the numbered examples refer to the preparation of the graft copolymer.

Referring to Table I, Method A and Method B refer to the tests described below with regard to simulated Tilden mine ore tailings.

Simulated Tilden Tailings: Tilden mine ore (1000 gm.-10 mesh) was ground with 1000 gm. water for 2 hours at 95 RPM in a rod mill containing 20 steel rods. The slurry was diluted to 1.6 percent solids and adjusted to pH 10 with sodium hydroxide.

Method A: Six 200 ml. portions of agitated slurry (described above) were placed in 250 ml beakers and stirred at 100 RPM on a Phipps and Bird gang stirrer. Test polymer (to achieve a final concentration of 1.1 ppm of polymer) was added, and the stirring was continued for 7 minutes at 100 RPM. The stirrer was stopped and after 5 minutes settling time, the clarities of the supernatant solutions were determined using a Hellige Turbidometer. These readings were reported in turbidity units (ppm $SiO_2$) using previously determined conversion data.

Method B: This method is essentially as described above for Method A, except that the supernatant clarity was measured using a Brinkman transmission probe. Clarity is reported in percent transmission.

Note that in Method A a low value is desired, and in Method B a high value is desired.

The value of $RV_{calc}$ shown in Table I was calculated as follows:

$$RV_{calc} = \frac{RV_b \times (Wt)_b + RV_s \times (Wt)_s}{(Wt)_b + (Wt)_s}$$

where $RV_b$ and $(Wt)_b$ represent the reduced viscosity and weight, respectively, of the polymer backbone used in the reaction; and $RV_s$ and $(Wt)_s$ represent the reduced viscosity and weight, respectively, of the polymer sidechain prepared independently under similar reaction conditions.

Flocculation of aqueous suspensions is generally effected by addition of graft copolymer, as such or in solution form, so as to achieve a final concentration of from 0.01 to 1000 ppm of graft copolymer based on the total weight of the suspension, i.e. the solution plus the suspended solids, the effective amount of graft copolymer flocculant varying with the characteristics and solids concentration of the suspension. Typically from about 0.05 to 200 ppm of flocculant is used for most applications. Specifically, for suspensions of iron ore tailings about 0.1 to 5 ppm of graft copolymer flocculant is generally an effective amount to achieve the desired degree of flocculation.

TABLE I

FLOCCULATION DATA FOR VARIOUS POLYMERS MEASURED AT 1.1 PPM POLYMER CONCENTRATION AND 5 MINUTES SETTLING TIME

| Examples | $RV_{obs}$ | $RV_{calc}$ | Backbone, % | Flocculation Results Method A (ppm $SiO_2$) | Method B (% transmission) |
|---|---|---|---|---|---|
| Blank Control | (no flocculant added) | | | >150 | <1 |
| Example A Control | 0.30 | — | 100 | >150 | 1 |
| Example B | 0.14 | — | 0 | 62 | 31 |
| Example 1 | 0.36 | 0.17 | 20.5 | 33 | 58 |
| Example 2 | 0.24 | 0.16 | 11.4 | 31 | 59 |
| Example 3 | 0.54 | 0.17 | 19.9 | 29 | 60 |
| Mixture A & B | 0.18 | 0.17 | 20.5 | 51 | 23 |
| Mixture A & B | 0.16 | 0.16 | 10.9 | 50 | 22 |
| Control Example C | 0.36 | — | 100 | 103 | — |
| Control Example D | 0.19 | — | 0 | 50 | — |
| Example 4 | 0.48 | 0.21 | 8.9 | 23 | — |
| Control Example E | 0.23 | — | 0 | 75 | — |
| Example 5 | 0.55 | 0.24 | 8.9 | 25 | — |
| Control Example F | 0.14 | — | 0 | 115 | — |
| Example 6 | 0.37 | 0.16 | 8.0 | 25 | — |
| Control Example G | 0.14 | — | 100 | 58 (a) | — |
| Control Example H | 0.14 | — | 0 | 135 | — |
| Example 7 | 0.36 | 0.14 | 9.9 | 31 | — |

(a) Settling time for this Example was 5 days.

Referring to Table I, control Example A gave no better results than the Blank. The polymer of Control Example B was a better flocculant than the polymer of A but far inferior to the polymers of Examples 1, 2 and 3 which were excellent flocculants. The physical mixtures of A and B comprised similar compositions as the graft copolymers of Examples 1–3 but were inferior flocculants.

The remaining Examples in Table I show the same effects. In each case the graft copolymer provided superior flocculation results relative to the polymeric backbone and sidechains from which they were formed.

The copolymer of Example 4 was superior to the polymers of Examples C and D; the polymer of Example 5 was superior to that of Example E; the polymer of Example 6 was superior to that of Example F; and the polymer of Example 7 was superior to that of Example H.

CONTROL EXAMPLE A

Preparation of NGP Backbone Polymer and Quaternization with Allyl Chloride

A two-liter flask fitted with a mechanical stirrer, thermometer, addition funnel, and condenser was charged with 86.1 gm (1.0 mole) of piperazine, 150 ml methanol, and 1.5 gm water. The resulting solution was stirred and heated to 50° C. in an oil bath. The oil bath was removed and 97.1 gm (1.05 moles) of epichlorohydrin was added with rapid stirring to the reaction mixture for a period of about 30 minutes while maintaining the reaction temperature at about 50° C. External heating was then applied to maintain a reaction temperature of 50° C. for 55 minutes at which time the reaction mixture was cooled to about 25° C. A solution of 40 sodium hydroxide in 268 gm methanol was prepared and 291 gm of this solution (0.95 mole NaOH) was added to the stirred reaction mixture over 20 minutes. After an additional 50 minutes, the reaction mixture was filtered to remove the salts which had formed. A reduced viscosity (RV) test gave 0.14 for the polymer in the filtrate solution. This solution was returned to the reaction flask and heated to 50° C. for 3.5 hours (RV of 0.23), stored overnight at 50° C., then heated to 40°–63° C. for 3.7 hours to obtain a polymer with 0.46 RV. Total yield was 542.7 gm solution containing about 27.6 percent solids (essentially quantitative).

Five hundred thirty-six gm of the polymeric solution was charged to the reaction flask (fitted as above) and 100 gm of water and 153 gm (2.0 mole) of allyl chloride were added. The reaction mixture was heated to reflux (about 43°–45° C.) for 6 hours. Excess allyl chloride and methanol solvent were then removed by distillation under reduced pressure on a rotary evaporator leaving 371 gm of polymer solution. Dimethylamine (22 gm of 40 percent aqueous solution, 0.2 mole) and 29 gm of water were added to the polymer solution and this reaction mixture was then heated at 50° C. for one hour. Excess dimethylamine was removed by distillation at reduced pressure on the rotary evaporator. The remaining methanol solvent was replaced by water in stepwise fashion, by successively adding increments of water to the reaction solution followed by incremental removal of the methanol by distillation on the rotary evaporator until the desired amounts of water and methanol were added and removed, respectively to give 407 gm of aqueous solution which was then diluted with water to produce 500 gm of solution containing about 38.2 percent solids, RV=0.30. The increase in polymer weight (about 43 gm) indicated about 28 percent quaternization of the nitrogens in the polymer.

CONTROL EXAMPLE B

Preparation of Side Chain Polymer from 1,3-Bis(dimethylamino)-2-propanol and 1,4-Dichloro-2-butene The reaction flask similar to that described in Control Example A was charged with 14.6 gm (0.1 mole) of 1,3-bis(dimethylamino)-2-propanol (>99 percent pure) and 30 gm water and the solution then heated to 40° C. 1,4-Dichloro-2-butene (12.5 gm, 0.10 mole, mixture of isomers) was added to the stirred reaction mixture over a period of about 12 minutes. The reaction mixture was then heated to 60° C. for two hours and at 70° C. for 10 minutes. The resulting polymer solution was diluted with 77 gm water to produce a solution containing 21.2 percent polymeric solids (essentially quantitative yield) with RV=0.14.

EXAMPLE 1

Preparation of Graft Copolymer by in situ Reaction

A two liter reaction flask fitted with a mechanical stirrer, condenser, thermometer, and dropping funnel was charged with 18.3 gm of the polymer solution prepared in Control Example A (7.0 gm polymer), 18.7 gm water, and 14.6 gm (0.1 mole) of 1,3-bis(dimethylamino)-2-propanol. The reaction mixture was stirred and heated to 40° C. and 12.5 gm (0.10 mole) of 1,4-dichloro-2-butene was then added over 10 minutes. The reaction mixture was heated to 60° C. for two hours and then to 70° C. for 10 minutes. The viscous reaction mixture was cooled and diluted with 106.4 gm water to give a solution containing 20.3 percent polymer (essentially quantitative yield) with RV=0.36.

EXAMPLE 2

Preparation of Graft Copolymer by in situ Reaction

The procedure of Example 1 was repeated using 9.15 gm of the polymer solution of Control Example A (3.5 gm polymer), 24.4 gm of water, 14.6 gm of 1,3-bis(dimethylamino)-2-propanol, and 12.5 gm of 1,4-dichloro-2-butene. The resulting reaction product solution was diluted with 92.4 gm of water to give a solution containing 19.9 percent polymer (essentially quantitative yield) with RV=0.22.

EXAMPLE 3

Preparation of Graft Copolymer by in situ Reaction with Adjustment of Stoichiometry The procedure of Example 1 was repeated, in part, on a larger scale. One hundred eight-three gm of the polymer solution of Control Example A (70 gm polymer), 187 gm of water, and 146 gm (1.0 mole) of 1,3-bis(dimethylamino)-2-propanol were charged to the reaction flask and heated to 40° C. One hundred twenty-five gm (1.0 mole) of 1,4-dichloro-2-butene was added over 45 minutes and the reaction mixture was then heated to about 57° C. over 40 minutes at which time the reaction mixture was very viscous. The reaction mixture was then diluted with 1000 gm water, heated to 38°–47° C. for 2.5 hours, and then allowed to stand at room temperature overnight. The reaction mixture contained gelled material. Eleven gm (0.075 mole) of di(tertiary)amine and 64 gm of water were added and the reaction mixture was then stirred and heated to 43°–54° C. for 2¼ hours. The cooled (25° C.), gel-free solution contained 20.3 percent polymer (essentially quantitative yield) with RV=0.54.

CONTROL EXAMPLE C

Preparation of Quaternized (Allyl Chloride and Methyl Chloride) Poly (N-glycidylpiperazine) Backbone Polymer A two-liter reaction flask fitted with a mechanical stirrer, thermometer, water cooled condenser and dropping funnel was charged with 142 gm poly(N-glycidylpiperazine) (RV=0.48) and 900 ml of absolute ethanol. Seventy-six and one-half gm (1.0 mole) of allyl chloride was added over a period of 15 minutes while the reaction was heated from 26° C. to 34° C. The reaction mixture was then maintained at 34°–40° C. for a period of 18 hours. The water cooled condenser was placed with a dry ice/acetone condenser and 71.6 gm (1.42 mole) of methyl chloride was then added to the reaction mixture over a period of 3 hours by means of a tube extending below the liquid surface of the mixture. The reaction mixture was then maintained at 33°–46° C. for 19 hours after which an additional 10 gm of methyl chloride (0.02 mole) was added, and the mixture was then maintained at a temperature of about 45° C. for an additional 24 hours. Excess allyl chloride, excess methyl chloride, and ethanol were distilled from the reaction mixture under reduced pressure on a rotary evaporator to produce 570.8 gm of solution containing 33.6 percent polymer. (The weight increase of 49.8 gm indicated that a minimum of 32.5 percent to, at most, 49 percent of the poly(N-glycidylpiperazine) nitrogens were in quaternary form.) Three hundred ten gm of this polymer solution was coagulated by addition to stirred acetone. The collected, dried polymer had an RV of 0.36.

CONTROL EXAMPLE D

Preparation of Side Chain Polymer from N,N'-Dimethylpiperazine and 1,4-Dichloro-2-butene A reaction flask similar to that described in Example 1 was charged with 28.6 gm (0.25 mole) of N,N'-dimethylpiperazine and 50 gm of water. Thirty-one and six-tenths gm (0.25 mole) of 1,4-dichloro-2-butene was added over a period of 40 minutes. At the end of the addition, the reaction temperature had risen to 50° C. and the reaction was then maintained at a temperature of 40°–50° C. for 36 hours. The reaction solution was then cooled and diluted with 50 gm of water to produce a solution containing 40.7 percent polymer (essentially quantitative yield) with an RV of 0.19.

EXAMPLE 4

Preparation of Graft Copolymer

A reaction flask similar to that described in Example 1 was charged with 3.0 gm of the quaternized polymer prepared in Control Example C, 30 gm of water, and 14.3 gm (0.125 mole) of N,N'-dimethylpiperazine. 1,4-Dichloro-2-butene (16.4 gm, 0.130 mole) was then added over a period of 7 minutes. The reaction mixture was heated at 60° C. for 2½ hours and then at 68° C. for 10 minutes. The cooled reaction solution contained 52.9 percent polymer with an RV of 0.36.

CONTROL EXAMPLE E

Preparation of Side Chain Polymer from 1,4-Diazabicyclo[2.2.2]octane and 1,4-Dichloro-2-butene The procedure of Control Example D was repeated using 28.3 gm (0.25 mole) of 1,4-diazabicyclo[2.2.2]octane, 60 gm of water, and 31.2 gm (0.25 mole) of 1,4-dichloro-2-butene. After addition of the dihalide, the reaction mixture was heated to a temperature of 40°–57° C. for 21 hours, cooled to 25° C., and diluted with 50 gm of water to give a solution containing 35.8 percent polymer with an RV of 0.23.

EXAMPLE 5

Preparation of Graft Copolymer

The procedure of Example 4 was repeated using 6.0 gm of the quaternized polymer prepared in Control Example C, 60 gm of water, 28.3 gm (0.25 mole) of 1,4-diazabicyclo[2.2.2]octane, and 32.8 gm (0.26 mole) of 1,4-dichloro-2-butene. After heating the reaction mixture as described in Example 4, the reaction mixture was cooled and diluted with 100 gm water to produce a solution containing 29.5 percent polymer with an RV of 0.55.

CONTROL EXAMPLE F

Preparation of Side Chain Polymer from 1,4-Bis(dimethylamino)butane and 1,4-Dichloro-2-butene The procedure of Control Example D was repeated using 36.4 gm (0.25 mole) of 1,3-bis(dimethylamino)butane, 40 gm of water, and 31.6 (0.253 mole) of 1,4-dichloro-2-butene. The dihalide was added to the other ingredients over a period of about 30 minutes. The reaction mixture was then heated to 60°–70° C. for 4 hours and cooled to room temperature to produce a solution containing 64.9 percent polymer with an RV of 0.14.

EXAMPLE 6

Preparation of Graft Copolymer

The procedure of Example 4 was repeated using 6.0 gm of the quaternized polymer from Control Example C, 60 gm of water, 36.4 gm (0.25 mole) of 1,3-bis(dimethylamino)butane and 32.8 gm (0.26 mole) of 1,4-dichloro-2-butene. After addition of the dihalide, the reaction mixture was heated as described in Control Example F. The resulting solution contained 52.3 percent polymer with RV=0.37.

CONTROL EXAMPLE G

Poly(N-glycidylpiperazine) Backbone Quaternized with Methyl Iodide

A reaction flask similar to that described in Example 1 was charged with 71 gm of poly(N-glycidylpiperazine) (RV=0.38), 400 ml of methanol and 100 gm of water. Methyl iodide (distilled, 156 gm, 1.10 mole) was added to the stirred mixture at 33° C. The reaction mixture was then heated for an additional 3 hours at 44°–48° C. Methanol and excess iodide were then removed by distillation under reduced pressure on a rotary evaporator; 100 gm of water was then added to the residue, and the polymer solution was coagulated by addition to a large excess of stirred acetone. The solid polymer was collected by filtration and dried at 30° under vacuum to give 168.6 gm of product with an RV of 0.14. (The weight increase of 97.6 gm indicated that about 69 percent of the backbone nitrogens were reacted).

CONTROL EXAMPLE H

Preparation of Side Chain Polymer from 1,3-Bis(dimethylamino)-2-propanol and 1,4-Dichloro-2-butene A reaction flask similar to that described in Example 1 was charged with 37.3 gm (0.25 mole) of 1,3-bis(dimethylamino)-2-propanol and 70 gm of water and then heated to about 40° C. 1,4-Dichloro-2-butene (31.6 gm, 0.25 mole) was added to the stirred reaction mixture over a period of 15 minutes and the reaction mixture was then heated to 45°–55° C. for 19 hours. The cooled reaction mixture contained 56.4 percent polymer with an RV of 0.15.

EXAMPLE 7

Preparation of Graft Copolymer

A reaction flask similar to that described in Example 1 was charged with 3 gm of the backbone polymer prepared in Control Example G, 30 gm of water, and 14.6 gm (0.10 mole) of 1,3-bis(dimethylamino)-2-propanol and the flask contents heated to 40° C. 1,4-Dichloro-2-butene (12.6 gm, 0.101 mole) was added to the stirred reaction mixture over a period of 10 minutes and the reaction mixture was then heated to a temperature of 60° C. for 2.5 hours and then to 70° C. for a few minutes. The cooled solution contained 47.4 percent polymer (greater than 94 percent yield) with an RV of 0.36.

CONTROL EXAMPLE I

Preparation of Poly(N-Glycidylpiperazine) Polymer

A reaction flask similar to that in Example 1 was charged with 345 gm (4.00 mole) of piperazine, 480 gm of methanol, and 6 gm water. The resulting solution was stirred and heated to 45° C. The heating mantle was removed and 363 gm (3.92 mole) of epichlorohydrin was added to the rapidly stirred reaction mixture over about four hours while maintaining the reaction temperature at 50°-55° C. External heating was then applied to maintain a reaction temperature of 50°-55° C. for one hour at which time the reaction mixture was cooled to about 25° C. A solution of 152 gm (3.80 mole) of sodium hydroxide in 650 gm methanol was added to the stirred reaction mixture over 25 minutes. After an additional 50 minutes, the reaction mixture was filtered to remove the salts which had formed. The filtered solution was returned to the flask and allowed to stand overnight. The solution was then heated at 55°-60° C. for about 2 hours, after which time 400 ml of water and 100 ml of 40 percent aqueous dimethylamine was added. The solution was held at 50° C. for an hour. After cooling, the methanol solvent was replaced by water by successively adding water to the reaction solution and flash distilling the methanol on a rotatory evaporatory to give 1660 gm of product solution containing about 35.2% solids, RV=0.32.

EXAMPLE 8

Preparation of Graft Copolymer

A reaction flask similar to that described in Example 1 was charged with 30 gm of the polymer solution prepared in Control Example I (10.4 gm polymer), 100 gm of water, and 51.1 gm (0.349 mole) of 1,3-bis(dimethylamino)-2-propanol. The reaction mixture was stirred and 36 gm of 1,4-dichloro-2-butene was added over 60 minutes while not allowing the temperature to rise above 60° C. One gram of 1,4-dichloro-2-butene was then added every hour for the next three hours while maintaining the temperature of the reaction mixture at about 55° C. One hundred milliliters of water was added and then three one-gram portions of 1,4-dichloro-2-butene was added during the next hour while maintaining the temperature at about 55° C. The mixture was then diluted with 200 ml of water and an additional 2.5 gm 1,4-dichloro-2-butene was added incrementally over the next three hours. The total amount of 1,4-dichloro-2-butene added was 44.5 gm (0.356 mole). The cooled solution contained 21.7 percent polymer with an RV of 0.56.

EXAMPLE 9

Preparation of Graft Copolymer

A reaction flask similar to that described in Example 1 was charged with 69 gm of poly(N-glycidylpiperazine) solution (23.9 gm polymer) (RV=0.37) prepared by the method described in Control Example I, 53 gm of water, and 51 gm (0.35 mole) of 1,3-bis(dimethylamino)-2-propanol. The reaction mixture was stirred and 35 gm of 1,4-dichloro-2-butene (0.8 mole-equivalents) was added over a period of 20 minutes while not allowing the temperature to rise above 60° C. Stirring was continued at a temperature of about 60° C. and within 20 minutes the material gelled. This example illustrates that the use of unquaternized polymer backbone at 22 weight percent resulted in a gelled product in contrast to previous Examples, such as Example 1, where no gelling occurred with the use of about 20 weight percent of partially quaternized polymer backbone.

What is claimed is:

1. A process for flocculating an aqueous suspension of finely divided particles which comprises treating the suspension with an effective amount of a water-soluble graft copolymer to achieve flocculation of said particles, said water soluble graft copolymer being comprised of polymeric units characterized by the general formula:

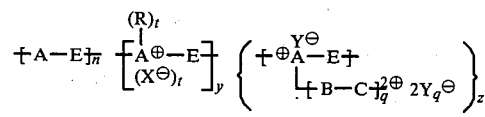

wherein n, y and z represent the relative molar equivalent fractions of each of the respective polymeric units in the graft copolymer, the sum of n, y and z being 1.0, the value of n varying from 0.00 to 0.99, the value of y varying from 0.00 to 0.99 and the value of z varying from 0.01 to 0.99; q is an integer greater than 1; A is the unit derived from at least one difunctional amine selected from the group consisting of primary amines and di(secondary)amines; t is an integer varying from 1 to 2; E is the unit obtained from a compound selected from the group consisting of epihalohydrins and diepoxides after its reaction with said difunctional amine; R is an organic radical derived from a quaternizing agent having the general formula RX, where X is the residual counter ion formed after quaternization; B is the unit derived from an organic dihalide having the general formula $BY_2$, where Y is $Cl^-$, $Br^-$ or $I^-$ with the proviso that such halogens are not attached to the same carbon atom; and C is the unit derived from an organic di(tertiary) amine after its reaction with said organic dihalide.

2. A process as in claim 1 wherein said finely divided particles are iron ore suspensions.

3. A process as in claim 1 wherein A is the unit derived from a primary alkyl or primary arylamine.

4. A process as in claim 1 wherein A is the unit derived from a di(secondary)alkyl or di(secondary)arylamine.

5. A process as in claim 1 wherein A is the unit derived from piperazine, E is the unit derived from epichlorohydrin, B is the unit derived from 1,4-dichloro-2-butene and C is the unit derived from 1,3-bis-(dimethylamino)-2-propanol.

6. A process as in claim 1 wherein the suspension is treated with an amount of said graft copolymer from about 0.05 to 200 ppm based on the total weight of the suspension.

* * * * *